United States Patent [19]

DeVries et al.

[11] 4,143,544

[45] Mar. 13, 1979

[54] FINGERPRINTING CRYSTALS

[75] Inventors: Robert C. DeVries, Burnt Hills; Roy E. Tuft, Guilderland Center, both of N.Y.

[73] Assignee: General Electric Company, Schenectady, N.Y.

[21] Appl. No.: 809,004

[22] Filed: Jun. 22, 1977

[51] Int. Cl.² ............................................. G01N 19/08
[52] U.S. Cl. ....................................................... 73/104
[58] Field of Search ............... 73/104, 432 R; 356/30, 356/32

[56] References Cited

U.S. PATENT DOCUMENTS 2,678,420  5/1954  De Forest et al. ..................... 73/104
3,162,040  12/1964  Cahen .................................... 73/104

Primary Examiner—Anthony V. Ciarlante
Attorney, Agent, or Firm—Jane M. Binkowsky; Joseph T. Cohen; Charles T. Watts

[57] ABSTRACT

A diamond or cubic boron nitride crystal containing growth discontinuities resulting from changes in the environment of the growing crystal and having at least one smooth outside surface which intersects the growth discontinuities is charged electrostatically, a fine powder is applied to the charged smooth surface and the applied powder produces a pattern on the charged surface which is a delineation of the intersected growth discontinuities.

10 Claims, 2 Drawing Figures

FINGERPRINTING CRYSTALS

The present invention relates to characterizing diamond or cubic boron nitride crystal enabling its identification thereafter.

When a crystal grows, it records in some structurally related way the events of its growth history. If the growth related structures can be revealed, it may be possible to reconstruct the unique growth history; but in addition, it may be possible to characterize the crystal.

There are various ways to reveal structure in crystals: by etching, by decoration of dislocations, by strain birefringence seen in polarized light, by cathodoluminescence, by different hardness and by X-ray topography. In the study of diamond, it is common to reveal growth bands by etching in molten nitrates, by cathodoluminescence or by X-ray topography. However, these ways of revealing crystal structure are of limited use and not practical because they either involve destructive testing, or do not characterize the crystal sufficiently, or require sophisticated expensive equipment.

The present invention makes it possible to reveal the detailed crystal structure by a technique which is based on the triboelectric effect or static electricity of diamond. The technique is simple, does not involve destructive testing, and applies to identification of gemstones and to the characterization of abrasive grain made by different manufacturers.

Briefly stated, the present process is directed to fingerprinting or characterizing a crystal selected from the group consisting of natural diamond, synthetic diamond and cubic boron nitride, wherein the crystal contains at least a significant amount of structural growth discontinuities resulting from fluctuations in conditions in contact with the growing crystal. Specifically, the present process comprises providing the crystal with at least one external surface having a surface area of at least 0.1 square millimeter which is at least substantially smooth and without significant elevational differences and which intersects at least a portion of its growth discontinuities, electrostatically charging the crystal so that at least the said smooth surface of the crystal is electrostatically charged, applying a powder to the said charged smooth surface and recording the pattern formed by the applied powder on the said charged smooth surface, said pattern being a delineation of the intersected growth discontinuities.

The product of the present invention is a fingerprint of a crystal selected from the group consisting of natural diamond, synthetic diamond and cubic boron nitride, said crystal containing at least a significant amount of growth discontinuities in its structure caused by fluctuations in conditions contacting the growing crystal and having at least one outside surface with a surface area of at least 0.1 square millimeter which is at least substantially smooth and which intersects at least a portion of said growth discontinuities, said fingerprint being composed of a powder pattern on said smooth surface of said crystal characterizing said crystal, said powder pattern being a delineation of said intersected growth discontinuities of said crystal, said powder ranging in particle size from submicron to about 45 microns.

The powder pattern formed by the present process is significantly broader than the growth discontinuities in the structure of the crystal.

Those skilled in the art will gain a further and better understanding of the present invention from the figures accompanying and forming part of the specification, in which.

Figure 1:
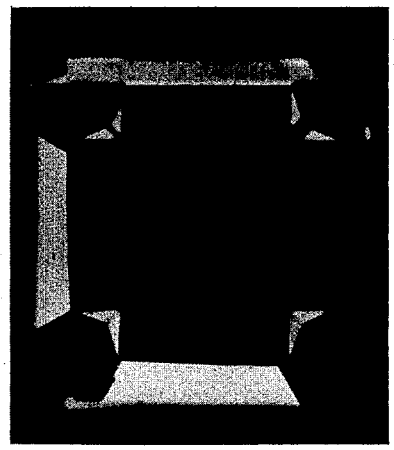
FIG. 1 is a photomicrograph (magnified about 15 X) of a man-made yellow diamond crystal having a cubo-octahedra morphology and showing a flat, smooth cube, i.e. (100) face.

The present crystal is a natural or synthetic diamond or a cubic boron nitride crystal and contains at least a significant amount of growth discontinuities in its crystal structure resulting from changes in the environment of the growing crystal. These growth discontinuities or non-uniformities in the crystal structure are caused by fluctuations in pressure and temperature to which the growing crystal is subjected as well as flutuations in specific composition. It is believed that at least a significant amount of such growth discontinuities are contained within all synthetic diamond crystals and all cubic boron nitride crystals and most natural diamond crystals. There are some natural diamond crystals, which grew under such homogeneous conditions that no growth discontinuities, are present.

In carrying out the present process, the diamond or cubic boron nitride crystal should have at least one pattern-producing surface, and preferably a plurality of such surfaces. Specifically, the crystal should have at least one pattern-producing surface which is an external, i.e. outside, surface with an area of at least 0.1 square millimeter, and preferably larger, which is smooth or at least substantially smooth, and which is free of elevational differences or at least substantially free of elevational differences, and which intersects at least a portion of the growth discontinuities of the crystal. This external pattern-producing surface may be a curved or convex surface, but preferably for easier recording of the powder pattern, it is a flat surface, and most preferably, it is a flat, totally level, plane surface. There is no maximum limit on the surface area of the present pattern-producing surface of the crystal. Also, there is no maximum limit on the size of the crystal.

In the present invention, by a crystal which contains at least a significant amount of structural growth discontinuities, it is meant an amount of growth discontinuities in its structure which will produce a powder pattern on the present pattern-producing surface or surfaces of the crystal which characterizes the crystal sufficiently to enable its identification thereafter. Also, the pattern-producing surface of the crystal intersects, i.e. passes through, at least a portion of these growth discontinuities. The extent, degree, or amount of such intersection should be at least sufficient to produce a powder pattern on the present powder-producing surface of the crystal which characterizes the crystal sufficiently to enable its identification thereafter.

By a powder pattern which characterizes the crystal sufficiently to enable its identification thereafter, it is meant a powder pattern which alone, or which along with its orientation with respect to some part or the rest of the crystal, characterizes the crystal sufficiently to enable its identification thereafter. Specifically, the present powder pattern is usually sufficiently unique and of sufficiently high resolution so that it alone characterizes the crystal sufficiently to identify it. However, in certain instances, the powder pattern alone may be insufficiently unique, for example, three parallel lines, or too small to provide sufficiently high resolution, but such powder pattern characterizes the crystal sufficiently to enable its identification thereafter when its orientation with respect to some part or the rest of the crystal is known or determined, or its location on the crystal is photographed. For example, such orientation may be with respect to the particular pattern-producing surfaces on which the powder pattern was formed, or it may be with respect to some inclusion or defect in the crystal.

In order that the characterizing powder pattern be formed in the present process, the surface of the crystal on which it is to be formed, i.e. the pattern-producing surface of surfaces, must intersect at least a portion of the growth discontinuities of the crystal. In an as-grown crystal, if the crystal grew by starting from a site within the crystal and grew outward in all directions, no external as-grown surface will intersect the growth discontinuities and such a crystal must be cut or polished to provide it with present pattern-producing surface. However, in an as-grown crystal where the crystal grew from a site which did not become totally overgrown, the external as-grown surface of the crystal containing that site would intersect the growth discontinuities and would be useful as a pattern-producing surface.

Generally, it will be necessary to shape at least one surface of an as-grown crystal of natural or synthetic diamond or synthetic cubic boron nitride to provide it with the present pattern-producing surface. By shaping, it is meant herein, for example, cutting, breaking, cleaving, abrading, polishing or any technique which penetrates into the interior of the crystal. The external as-grown surface of the crystal can be shaped to produce a pattern-producing surface which may be at an angle or parallel to such external as-grown surface. Usually, the probability of the shaped surface intersecting the maximum number of growth discontinuities in the crystal is enhanced by shaping the surface to penetrate as deeply into the interior of the crystal as possible. The resulting shaped pattern-producing surface can be flat or curved and at an angle, or transverse or parallel to major growth surfaces.

In an octahedron shaped diamond crystal the maximum flat area would be on the (100) plane through the girdle of the octahedron. In the practice of diamond gemstone production from naturally occurring octahedra, it is common to saw on the (100) plane somewhat above the girdle so as to produce one larger and one smaller stone from the same original crystal. The cut (100) type surfaces of the resulting crystals become the large table facet of a brilliant cut and are nearly ideal pattern-producing surfaces since they cut deeply into the original crystal and thereby increase the probability of intersecting nearly the maximum number of growth discontinuities that may exist in the crystal. In addition, the crown and pavilion facets of a brilliant cut can also intersect growth discontinuities in the crystal.

Man-made diamonds of gem quality are grown on a seed positioned so that growth is upward from the seed. In this case growth discontinuities can be intersected by shaping into the crystal in a plane parallel to the surface that contained the seed. The orientation of the resulting shaped surface can be anything in principle but in practice is more likely {100} or {111}.

For small diamond crystals like cubo-octahedral abrasive grain, shaping into the crystal in a plane parallel or perpendicular to the major external surface will intersect the growth discontinuities if they exist.

Cutting of the diamond or cubic boron nitride crystal to produce the required outside surface which intersects the growth discontinuities of the crystal, i.e. the present powder pattern-producing surface of the crystal, can be carried out by a number of techniques, such as by cleaving or sawing the crystal. If desired, the crystal can be shaped by grinding usually be means of a diamond impregnated grinding wheel. A smooth polished surface can be produced mechanically by polishing the crystal on a cast iron lap or scaife. In a preferred embodiment of the present invention, the crystal is mechanically polished to provide at least the pattern-producing surface or surfaces with a smooth surface which is free or at least substantially free of any elevational differences. After such mechanical polishing, the crystal should be cleaned with solvent such as acetone or isopropyl alcohol and dried to remove any adherent particles or dust which may interfere with the present powder pattern formation.

If desired, the pattern-producing surface or surfaces of a crystal can be determined empirically. For example, the entire crystal can be charged electrostatically, the present fine powder applied or dusted onto the charged crystal and the particular surface or surfaces of the charged crystal on which the present characterizing powder pattern forms determined.

In carrying out the present process, the crystal is electrostatically charged at least sufficiently to produce a characterizing powder pattern in accordance with the present process. Preferably, before the crystal is electrostatically charged, it is cleaned with solvent such as acetone or isopropyl alcohol and dried to remove any adherent particles and dust which may interfere with the present powder-pattern formation. The crystal can be electrostatically charged so that at least the pattern-forming surface of the crystal is charged, but preferably, the entire crystal is electrostatically charged.

The crystal can be electrostatically charged by a number of techniques. In one technique, the crystal is rubbed with an insulating material. By an insulating material it is meant a material which permits the passage of the lines of force of an electrostatic field but does not conduct electric current. Preferably, the insulating material is a continuous pliable material. Representative of the insulating materials useful in the present process are cotton cloth, silk, paper, rubber and plastics.

In another technique, the crystal is electrostatically charged by pressing an adhesive surface of tape on it and stripping it off rapidly. This technique also can serve as a simultaneous cleaning process for the surface to be studied.

Preferably, the crystal is charged electrostatically by subjecting it to an electric field. For example, the crystal can be placed in an electric field provided by a corona discharge, which is an electric discharge resulting from a partial electric breakdown in the gas or air surrounding a wire at high potential.

The powder used to form the pattern in the present process, i.e. the pattern-forming powder, can be an insulating powder, semiconducting or metallic, or mixtures thereof. Representative of these powders are talc, flour, polymer, $Al_2O_3$, $ZnS$, $Pb_3O_4$, $CrO_2$, $Fe_2O_3$, $Cr_2O_3$, nickel, iron, and graphite.

The pattern-forming powder should be non-aggregative in order that it may form reproducible patterns of satisfactory resolution. Usually the smaller the particle size of the powder, the more refined is the resolution of the resulting pattern. For best results, the powder has a particle size ranging from submicron to about 5 microns. However, powder comprised of a mixture of sizes ranging up to about 45 microns may also be used providing at least about 5% by volume, and preferably higher portions of such a powder, is composed of particles ranging from submicron to about 10 microns in size. The large particles do not give good resolution and may not stick. In a mixed particle size powder the finer sizes tend to be the pattern producing particles.

The present powder can be applied to the charged crystal by a number of techniques. For example, it can be sprinkled or dusted onto the charged crystal by means of, for example, a salt shaker, blower, or syringe. The powder is applied at least to the entire charged pattern-producing surface, but preferably, it is applied to the entire exposed surface area of the charged crystal. For example, if the crystal is mounted in a ring or some type of holder, the powder is applied preferably to the entire exposed external surface area of the crystal. It appears that certain forces within the charged crystal attract the powder forming it into a powder pattern thereon. Alternatively, the charged crystal can be dipped into the powder, and the excess powder shaken off or otherwise removed to reveal a powder pattern. In another technique, a fast-drying liquid dispersion of the powder can be sprayed or otherwise deposited on the charged crystal forming a wet coating thereon, which as it dries, frees the dry powder to form into a pattern on the charged crystal.

The powder pattern formed on the charged crystal in the present process frequently is an arrangement of lines. The powder forming the pattern on the charged crystal clings to it apparently being held in place by charged forces of the crystal. Excess powder which may deposit on the crystal, i.e. powder which does not form part of the powder pattern, does not show this clinging effect, and since there is no attraction between it and the crystal, it can be removed by a number of techniques without affecting the powder pattern. For example, it can be gently blown off or shaken off the charged crystal. If desired, excess powder can be removed from the charged crystal by placing the charged crystal within a stream of air flowing at a rate sufficient to remove or carry off the excess powder but not so high rate as to have any effect on the powder pattern.

In one embodiment of the present invention, the crystal is electrostaticaly charged and the powder is applied thereto simultaneously, i.e. the powder-pattern is developed at the same time the crystal is being charged. For example, while the crystal is being electrostatically charged in a corona discharge, the powder can be sprayed or otherwise applied to the crystal. This is an advantage if conditions are such that rapid leakage of the charge might take place, such as under high humidity, between the charging and dusting steps.

In yet another embodiment the crystal is electrostatically charged in a positive or negative field produced by ionization of air molecules by corona discharge. As a result, the pattern-producing surface of the resulting charged crystal may be positively charged or negatively charged. When powder is applied according to the present process to a crystal with pattern-producing surfaces which are positively charged, and subsequently applied to the same crystal with the pattern-producing surfaces negatively charged, the resulting powder patterns bear a relationship to each other that is similar to positive and negative photographic prints. The patterns are geometrically the same but the concentrations of the powder is reversed. Such a combination of patterns is also unique to each crystal.

Also, some powders have a tendency to be positively charged and others have a tendency to be negatively charged. Thus, the powder pattern produced by one powder on a positively charged surface of a crystal can be the same as the powder pattern produced by another powder on the same surface of the crystal but negatively charged, indicating that the powders are oppositely charged initially, and in such instance the concentration of a powder in a pattern will be a function of both the sign of the charge on the crystal surface and on the particles.

Since many powders frequently have a tendency to be composed of a mixture of positively charged and negatively charged particles, an electric field is useful in the present process to produce patterns of high resolution by passing such a powder, usually in the form of a dust cloud, through the electric field prior to deposition on the charged crystal. The field extracts particles from the dust cloud of charge opposite to it. For example, the electrode for establishing the electric field may be in the form of a metallic screen located close to and under the mounted crystal providing the field between it and the crystal and the powder is passed through the screen and through the field to deposit on the charged crystal. Specifically, when the crystal is positively charged, the electrode would be negatively charged providing a negatively charged field to remove particles of positive charge from the dust cloud leaving particles of negative charge to deposit on the positively charged sufaces of the crystal. Under these conditions the particles of negative charge may be further charged and accelerated by the field to deposit on the crystal. The powder pattern on the crystal is enhanced by the resulting increase in the proportion of particles of negative charge.

The powder pattern produced by the present process can be recorded by a number of techniques. For example, it can be recorded photographically. It is also possible to preserve and record the present powder pattern by placing a piece of transparent adhesive tape, for example Scotch tape, over the pattern. When pressed down smoothly, the powder pattern is removed and preserved by the tape when it is stripped off the crystal. The tape can then be placed on a card or rigid surface or on another piece of tape for preservation. If the card or surface is transparent it is easier to make comparisons of patterns by overlay on a light box or by projection onto a screen.

The powder pattern formed in accordance with the present process is recorded so that it is available for comparison with subsequently formed powder patterns. Powder patterns produced by the present process can be compared by a number of techniques. For example, a powder pattern produced in the same manner on the same powder-producing surface or surfaces of the same crystal as a recorded powder pattern should be the same or at least sufficiently or substantially the same as the recorded powder pattern so as to identify the particular crystal. Alternatively, identification of the crystal can be made by such comparison of the powder patterns along with their location or orientation with respect to some part or the rest of the crystal. Specifically, comparison can be made by comparing photographs of the powder pattern-carrying crystals. Alternatively, comparisons can be made visually, preferably under a microscope. Also, comparisons can be made by superimposing one powder pattern onto another. Projection of the powder patterns on a wall magnifies them substantially and produces projected patterns of high resolution.

A fluorescent or colored powder aids in seeing the patterns on the crystal surface. Specifically, it is particularly preferred to use a powder of a color which gives a contrasting color when deposited on a crystal of a particular color, i.e. or opaque on a transparent crystal.

The present invention is useful in characterizing abrasive grain as well as gemstones. The present process is non-destructive to the crystal or to the polished surface of the crystal and a spray or powder pattern of the table of a gem diamond would be like a fingerprint — no two alike.

The invention is further illustrated by the following examples where the procedure was as follows unless otherwise noted:

All polishing of the crystal was carried out mechanically on an iron scaife.

In each instance before electrostatically charging a crystal, the crystal was cleaned to remove any powder or dust which might be present on its surfaces. To clean the crystal it was dipped or swabbed in acetone or isopropyl alcohol and dried in air or in jet of air or inert gas.

To electrostatically charge a crystal by corona discharge, a corona discharge apparatus was used which included a wire passing longitudinally through the central portion of an horizontally positioned copper tubular sheath having a diameter of about one inch and a length of about 3 inches which had an opening along its bottom portion. The crystal, when unmounted, was mounted either on a metal plate using electrically conducting silver paste to adhere it to the plate, or it was held tightly in three-prong metal tweezers, or embedded in solder in a metal holder, or it was mounted in the prongs of a metal ring. An electrode was attached to the metal plate, or to the tweezers or to the metal ring, the electrode being connected electrically to one side of the D.C. field by which the corona charge is developed. The mounted crystal was positioned within the opening facing the wire. The wire was then charged by a D.C. field of 5000 volts for a few seconds at least but usually less than 1 minute, causing the crystal to be subjected to a charged field and to become electrostatically charged. The charge appeared to be developed instantaneously.

The suspension of nickel powder in liquid used was comprised of nickel powder suspended in an insulating liquid, i.e. a trichlorofluoroalkane, under pressure and sold under the trademark Kyread. This was a fast drying suspension which dried rapidly, usually from less than a second to 2 seconds after application. Examination of the resulting dry nickel powder showed it to be non-aggregative and free-flowing. The nickel powder ranged in size from about 1/2 micron to about 1 micron.

All of the examples were carried out at room temperature in air.

The polymer powder used was a fine, free-flowing, non-aggregative powder, submicron in size, sold under the trademark Xerox 125 blue toner.

The graphite powder used had a size less than 44 microns and about 25% by volume of the powder ranged in size from submicron to about 5 microns. This powder was free-flowing and non-aggregative.

When a powder-pattern was preserved and recorded on adhesive tape, this was carried out by pressing down the adhesive surface of a clear transparent tape, i.e. Scotch tape, smoothly over the entire powder-pattern, which was then removed and preserved by the tape when it was stripped off the crystal.

EXAMPLE 1

A natural diamond gemstone of round briliant cut mounted in a ring setting with four prongs was used. The area of the table facet of the gemstone, i.e. the principal pattern-producing surface of the gemstone, was approximately 5.7 square millimeters. This pattern-producing surface was flat and smooth and did not appear to have any elevational differences.

All of the exposed crown surfaces of the gemstone were rubbed with cotton cloth for a few seconds to electrostatically charge the crystal. A suspension of nickel powder in liquid was sprayed on all of the exposed surfaces of the charged crystal forming a wet continuous coating thereon which dried rapidly.

The resulting dry nickel powder on the table of the gemstone formed a distinctive pattern which extended nearly across the entire surface of the table. The pattern was comprised largely of an array of straight lines crossing each other at certain points. This powder-pattern was preserved and recorded photographically and then on adhesive tape.

EXAMPLE 2

In this example the diamond gemstone ring of Example 1 was used. The gemstone was electrostatically charged by corona discharge. The ring was then removed from the electric field and a suspension of nickel powder in liquid was sprayed on the charged crystal forming a wet coating over the entire exposed surface area of the charged crystal which dried rapidly.

The resulting dry nickel powder formed a distinctive pattern on the table of the gemstone. A comparison of this powder pattern with the pattern recorded in Example 1 showed them to be the same.

EXAMPLE 3

In this example an unmounted colorless man-made gem quality diamond crystal weighing 0.208 gram was used. One external as-grown surface, i.e. the {100} seeded surface of this diamond had been mechanically polished to remove about a 30 mil thickness of the diamond to produce a polished surface parallel to the as-grown surface. The final weight of the crystal was 0.172 gram. This polished surface was smooth, flat and free of significant elevational differences. It had an external surface area of about 1.7 square millimeters.

The entire polished surface of the crystal was rubbed against silk cloth for a few seconds. The resulting electrostatically charged crystal was then sprayed with the liquid dispersion of nickel powder forming a wet continuous coating thereon which dried rapidly. The resulting dry nickel powder formed into a distinctive pattern which extended over the entire polished surface. The pattern was comprised largely of an arrangement of lines crossing each other at certain points. The powder-pattern was recorded on adhesive tape.

EXAMPLE 4

The man-made crystal of Example 3 was used in this example. It was electrostatically charged in the same manner disclosed in Example 3. The entire polished surface of the charged crystal was then dusted with graphite powder by spraying the powder thereon with a syringe.

The charged crystal was shaken manually to shake off excess graphite powder leaving a distinctive graphite powder-pattern on the polished surface. This powder-pattern was substantially the same as that recorded in Example 3, but because of the larger size of the graphite powder, it did not have as high a resolution as the pattern of Example 3.

EXAMPLE 5

The diamond crystal used in this example was the same as that used in Example 3. The crystal was electrostatically charged by rubbing on silk cloth for a few seconds. Powdered polymer was dusted onto the charged crystal by puffing it thereon with a syringe. The powder formed into a distinctive pattern on the polished surface of the crystal. A comparison of this pattern with the pattern recorded in Example 3 showed them to be the same.

EXAMPLE 6

A man-made yellow diamond crystal of approximately one carat was mounted in solder in a metal holder and an as-grown surface thereon was polished approximately on the {100} plane with about a 20 mil thickness of the crystal being removed. The external surface area of the resulting polished surface was about 16 square millimeters. The polished surface was smooth, flat and did not have any significant elevational differences.

The polished surface of the crystal in the metal mount was electrostatically charged by rubbing it on cloth for a few seconds. The resulting charged crystal was then sprayed with a suspension of nickel powder in liquid forming a wet coating over the entire polished surface which dried rapidly. The resulting dry nickel powder formed into a distinctive pattern which was comprised largely of an array of lines crossing each other at certain points extending over the entire polished surface of the crystal. This pattern was recorded photographically.

EXAMPLE 7

The diamond crystal of Example 6 was used in this example. The crystal was charged electrostatically by rubbing on cloth and a nickel powder pattern formed on the polished surface thereof in the same manner disclosed in Example 6. The pattern was recorded on adhesive tape. A comparison of this pattern adhered to the adhesive tape with the pattern recorded photographically in Example 6 showed them to be the same.

EXAMPLE 8

The crystal of Example 6 was used in this example. The polished surface of the crystal was electrostatically charged by contacting it with the adhesive surface of a tape and stripping the tape off rapidly. The charged crystal was sprayed with a suspension of nickel powder in liquid forming a wet coating over the entire area of the polished surface which dried rapidly. The resulting dry nickel powder formed a pattern on the polished surface which was the same as the pattern recorded in Example 6.

EXAMPLE 9

The crystal of Example 6 was used in this example. It was adhered to a metal plate by silver paste and electrostatically charged by means of a corona discharge. The resulting charged crystal was removed from the electrostatic field and sprayed with a suspension of nickel powder in liquid forming a wet continuous coating over the entire area of the polished surface of the crystal which dried rapidly. The resulting dry nickel powder formed into a pattern on the polished surface which was the same as the pattern recorded in Example 6.

EXAMPLE 10

A colorless man-made polished diamond gemstone of round 58 facet brilliant cut and weighing 0.28 carats was cleaned in isopropyl alcohol and dried in a blast of gas from a can of compressed fluorocarbon. The crystal was mounted with the crown up in a small depression in a metal plate using a conducting silver paste. The crystal was electrostatically charged with a positive corona discharge and the resulting charged crystal then sprayed with a suspension of nickel powder in liquid which dried rapidly. The resulting dry nickel powder formed into a distinctive pattern on the table facet, which had a smooth surface area without significant elevational differences of about 4 square millimeters and on some of the crown facets each of which had a smooth area without significant elevational differences of about 0.15 square millimeter. This pattern was recorded by the tape technique.

The crown portion of the mounted crystal was cleaned again with a swab of isopropyl alcohol and dried in a blast of gas from a can of compressed fluorocarbon, and then recharged with a positive corona discharge and resprayed with the nickel suspension. A comparison of the resulting nickel powder pattern on the table facet and the crown facets with the pattern recorded on tape showed them to be the same.

The crown portion of the mounted crystal was cleaned again with a swab of isopropyl alcohol and dried in a blast of gas from a can of compressed fluorocarbon, and then recharged with a positive corona discharge and sprayed with polymer powder from an atomizer. A comparison of the resulting polymer powder pattern on the table facet and the crown facets with the pattern recorded on tape showed them to be the same.

The crystal was then removed from the mount, cleaned in acetone to remove the silver paste, dried in a blast of gas from a can of compressed fluorocarbon and remounted in the depression in the metal plate but this time with the pavilion facets exposed. The crystal was electrostatically charged with a positive corona discharge and the resulting charged crystal then sprayed with a suspension of nickel powder in liquid which dried rapidly. The resulting dry nickel formed into a distinctive pattern on these facets which was reproducible. This pattern was not the same as on the table-crown pattern but was related to it in three dimensions and was itself unique to this crystal. The combination of the two unique patterns is additional identification of this crystal. The recording of the pattern on the pavilion facets is difficult by means of the tape technique because of the steep cone shape but the pattern can be easily recorded photographically.

EXAMPLE 11

The crystal of Example 10 was mounted by mounting it crown up with silver paste on a metal plate and electrostatically charged by corona discharge. The charged crystal and plate were removed from the electrostatic field and placed within the upper portion of a box with the crown facing downwardly. An electric field of about 1000 volts was generated within the box from a grid to the plate on which the crystal was mounted, the grid being positioned under the crystal in the lower portion of the box. Powdered polymer was dusted onto the charged crystal by spraying it from an atomizer through the bottom portion of the box and through the grid. The powder became charged on contact with the electric field before contacting the electrostatically charged crystal.

Examination of the resulting dusted crystal showed that a distinctive powder-pattern was developed on the table facet and on some of the crown facets. A photograph was taken of the crystal showing the patterns thereon. This pattern was the same as that recorded for the crown of the crystal in Example 10.

EXAMPLE 12

Three octahedrally shaped natural diamond crystals were polished down perpendicular to one of the points of each of the octahedra to produce a {100} plane through each of the crystals just above the girdle of the octahedra. The polished plane of each crystal was smooth and without significant elevational differences. The polished plane of one crystal had an area of about 3 millimeters $\times$ 3½ millimeters; the polished plane of the second crystal had an area of about 3 millimeters $\times$ 2 millimeters; and the polished plane of the third crystal had an area of about 1½ millimeters $\times$ 3 millimeters.

With the polished plane up, each of the three crystals was mounted with silver paste on a metal plate and electrostatically charged simultaneously by corona discharge. After removal from the field, the three electrostatically charged crystals were sprayed with polymer powder from an atomizer. The powder formed a unique pattern on each charged crystal, each pattern being different from the other revealing the particular growth discontinuities in in each crystal. Specifically, two crystals showed a simple pattern of a line inside the outer rim of the crystals; the third crystal showed a pattern which was more complex with some resemblance to the patterns seen in man-made crystals.

The polished planes of the crystals were cleaned, recharged in the same manner and sprayed with a suspension of nickel powder in liquid. The resulting dry nickel powder formed into a distinctive pattern on the polished plane of each crystal which was the same as that formed by the polymer powder on that surface.

This example illustrates the use of the techniques to reveal patterns in several crystals simultaneously.

EXAMPLE 13

A thin slab of a single crystal of man-made diamond which was about 0.0348 inch thick, about 0.220 inch long and about 0.210 inch wide was used. The crystal weighed 0.744 gram. Its opposite sides or surfaces were polished, flat, smooth and free of significant elevational differences with each surface having an area of about 0.3 square centimeters.

The crystal slab was electrostatically charged by corona discharge with one side of the crystal facing the wire providing the electric field. The charged crystal was then removed from the field and the crystal side which had been facing the wire was sprayed with polymer powder from an atomizer. The powder formed a distinctive pattern on this side of the crystal which was recorded on adhesive tape. The entire procedure of electrostatically charging and spraying with powder was repeated with the opposite side of the crystal slab producing a distinctive powder-pattern which was also recorded on adhesive tape.

A comparison of the two patterns showed them to be the same geometrically but different in dimensions as expected for two different sections of a crystal.

EXAMPLE 14

The procedure of Example 13 was repeated but using a suspension of nickel powder in liquid. The nickel powder patterns formed were the same as their recorded counterparts in Example 13.

This type of thin slab of single crystal is typical of what might be used for optical windows, e.g. for a $CO_2$ laser, and the present powder-pattern process would be useful in characterizing the inhomogeneities of the crystal.

EXAMPLE 15

A thin plate of diamond which was 0.025 inch $\times$ 0.230 inch was cut from a man-made colorless crystal. Its opposite sides or surfaces were {100} planes and were polished, flat, smooth and free of significant elevational differences.

The diamond plate was held with three-prong tweezers and cleaned in isopropyl alcohol and after drying, it was electrostatically charged while held in the tweezers by rubbing with cloth. Both sides of the crystal were electrostatically charged almost simultaneously by this process.

The charged crystal plate was dusted on both sides, i.e. its opposite large sides, simultaneously with polymer powder from an atomizer, and two distinct, different, but related patterns were produced simultaneously on these sides.

EXAMPLE 16

A single crystal of cubic boron nitride, about 2½ millimeters $\times$ 3 millimeters, was set in a resin used for metallographic mounts and after adhering of the resin, the crystal was polished to produce a flat smooth surface of unknown orientation intersecting the interior of the crystal, a few mils from the original as-grown surface. The polished surface was free of significant elevational differences and had an area of about 8.75 square millimeters.

The polished surface of the crystal was electrostatically charged by rubbing it with a wool cloth. The suspension of nickel powder in liquid was immediately sprayed on the charged surface, and the resulting dry nickel powder formed a unique pattern of oriented angular regions were sprayed on the surface. The pattern was recorded on the adhesive tape.

The same pattern was reproduced on the polished surface immediately afterwards by cleaning the polished surface, rubbing it on wool and spraying it with the nickel powder suspension in the same manner. This pattern was recorded by using adhesive tape. Immediately after stripping the adhesive tape from the crystal which removed the powder-pattern leaving a clean surface, the polished surface was resprayed with the suspension of nickel powder in liquid and the resulting dry nickel powder formed the same pattern again on the polished surface since this surface was recharged when the adhesive tape was stripped off of it.

The crystal was then cleaned in isopropyl alcohol, dried in air but not recharged. Upon spraying the polished surface with the suspension of nickel powder in liquid, no pattern developed, i.e. there was no evidence on the polished surface of any discontinuities associated with the dust pattern.

The crystal was then cleaned and its polished surface was electrostatically charged by rubbing it with thin tissue paper. Polymer powder was sprayed from an atomizer on the charged electrostatically surface forming a pattern which was the same as that recorded on adhesive tape.

The crystal was then cleaned and its polished surface electrostatically charged by rubbing it with thin tissue paper. Graphite powder was then dusted from a syringe onto the electrostatically charged surface revealing a pattern which was the same as that recorded on adhesive tape.

EXAMPLE 17

Figure 2:
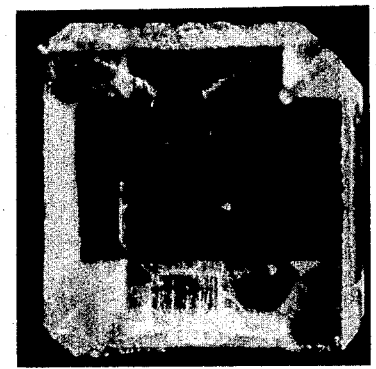
FIG. 2 is a photomicrograph (magnified about 15 X) showing the diamond crystal of FIG. 1 with a powder pattern formed on the (100) face produced in accordance with the present process.

A yellow man-made diamond crystal was polished about 30 mils into the crystal parallel to the {100} seed face to remove the seeded area. The polished surface measured about 5 millimeters × 5 millimeters and is shown in FIG. 1. This surface was electrostatically charged by rubbing it with cloth. Upon spraying the charged crystal with a suspension of nickel powder in liquid, the resulting dry nickel powder formed the distinctive "dust" pattern seen in FIG. 2. This pattern was reproducible upon repeating the process.

EXAMPLE 18

The crystal of Example 6 was used in the example. The polished surface of the crystal was electrostatically charged by rubbing it on wool. The charged crystal was sprayed with a suspension of nickel powder in liquid forming a wet coating over the entire area of the polished surface which dried rapidly. The resulting dry nickel powder formed into a pattern on the polished surface which was recorded on adhesive tape.

The same pattern was reproduced on the polished surface immediately afterwards by cleaning the polished surface, rubbing it on wool and dusting it with graphite powder from a syringe.

The graphite pattern was recorded by using adhesive tape. Immediately after stripping the adhesive tape from the crystal which removed the powder pattern leaving a clean surface, the polished surface was resprayed with the suspension of nickel powder in liquid and the resulting dry nickel powder formed the same pattern again on the polished surface since this surface was recharged when the adhesive tape was stripped off of it.

The crystal was then cleaned in isopropyl alcohol, dried in air, but not recharged. Upon spraying the polished surface with the suspension of nickel powder in liquid, no pattern developed.

EXAMPLE 19

The crystal of Example 6 was used in this example. The polished surface of the crystal was electrostatically charged by rubbing it with tissue paper.

A well-mixed powder consisting of about equal volumes of orange lead oxide ($Pb_3O_4$), having a particle size of about 10 microns and polymer powder was dusted onto the charged surface of the crystal with a syringe.

The pattern formed by the mixed powder was the same as that formed under the same conditions with polymer powder alone or with the orange $Pb_3O_4$ alone.

EXAMPLE 20

The man-made crystal of Example 10 was used in this example. The crystal was charged electrostatically by corona discharge with the crown surface of the crystal facing the wire of the corona discharge apparatus. The charged crown surfaces of the crystal were then sprayed with polymer powder from an atomizer which revealed the pattern outlining the growth stages of the crystal.

The crystal was then turned over and electrostatically charged by corona discharge with the pavilion facets facing the wire of the corona discharge apparatus. The charged pavilion facets of the crystal were then sprayed with graphite powder from a syringe which revealed a unique pattern on the pavilion facets of the crystal.

The use of powders of different color on the same crystal was demonstrated by this example. This technique has proved useful in comparing the two patterns on opposite faces of a thin transparent crystal.

EXAMPLE 21

The man-made diamond crystal of Example 3 was used in this example. The polished surface of the crystal was charged electrostatically by corona discharge. Polymer powder was sprayed from an atomizer on the charged surface of the crystal and revealed a distinctive pattern which was the same as formed in Example 3. Without removing the pattern, the crystal was recharged electrostatically by corona discharge and resprayed with polymer powder two more times in the same manner. After each charging and spraying, the pattern was intensified and enhanced.

EXAMPLE 22

The man-made diamond crystal of Example 3 was used in this example. The crystal was held in a three-prong metal tweezers and with the polished surface of the crystal facing the corona wire it was charged by corona discharge. The suspension of nickel powder in liquid was sprayed on the charged surface, and the resulting dried nickel powder formed the distinctive pattern on this surface.

Using metal tweezers which grip the crystal tightly is a convenient fast method for handling crystals, and several tweezers-held crystals can be mounted simultaneously under the corona discharge.

What is claimed is:

1. A process for characterizing a crystal selected from the group consisting of natural diamond, synthetic diamond and cubic boron nitride, said crystal containing at least a significant amount of structural growth discontinuities caused by fluctuations in the conditions contacting the growing crystal which comprises providing said crystal with at least one external surface having a surface area of at least 0.1 square millimeter which is at least substantially smooth and without significant elevational differences and which intersects at least a portion of said growth discontinuities, electrostatically charging said crystal so that at least said smooth surface of said crystal is electrostatically charged, applying a powder to said charged surface forming a powder pattern on said charged surface, said powder having a particle size ranging from submicron to about 45 microns, said pattern being a delineation of said intersected growth discontinuities.

2. A process for characterizing a crystal according to claim 1 wherein said crystal is electrostatically charged and said powder is applied simultaneously.

3. A process for characterizing a crystal according to claim 1 wherein said external surface is mechanically polished before said crystal is electrostatically charged.

4. A process for characterizing a crystal according to claim 1 wherein said crystal is electrostatically charged by corona discharge.

5. A process for characterizing a crystal according to claim 1 wherein said powder has a particle size ranging from submicron to about 5 microns.

6. A process for characterizing a crystal according to claim 1 wherein said powder is selected from the group consisting of an insulating powder, a semiconducting powder and a metallic powder.

7. A fingerprint of a crystal selected from the group consisting of natural diamond, synthetic diamond and cubic boron nitride, said crystal containing at least a significant amount of growth discontinuities in its structure caused by fluctuations in conditions contacting the growing crystal and having at least one outside surface with a surface area of at least 0.1 square millimeter which is at least substantially smooth and which intersects at least a portion of said growth discontinuities, said fingerprint being composed of a powder pattern produced by the process of claim 1.

8. A photograph of the fingerprint of said crystal of claim 7.

9. The fingerprint of said crystal of claim 7 wherein said powder pattern is adhered to the adhesive surface of a transparent tape.

10. The fingerprint of said crystal of claim 7 wherein said powder ranges in particle size from submicron to 5 microns.

* * * * *